United States Patent [19]

Margel

[11] Patent Number: 4,861,705

[45] Date of Patent: Aug. 29, 1989

[54] METHOD FOR REMOVING COMPONENTS OF BIOLOGICAL FLUIDS

[75] Inventor: Shlomo Margel, Rehovot, Israel

[73] Assignee: Yeda Research and Development Company, Ltd., Rehovot, Israel

[21] Appl. No.: 922,021

[22] Filed: Oct. 22, 1986

Related U.S. Application Data

[62] Division of Ser. No. 462,315, Jan. 31, 1983, abandoned.

[51] Int. Cl.$^4$ ............................................... A01N 1/02
[52] U.S. Cl. ........................................ 435/2; 435/174; 435/181; 435/803; 210/635; 210/661; 210/679; 210/927; 436/528; 436/531; 436/532; 436/541; 530/412; 530/413; 530/415
[58] Field of Search ................... 435/2, 174, 181, 803; 436/528, 532, 541, 531; 210/635, 661, 679, 927; 530/412, 413, 415

[56] References Cited

U.S. PATENT DOCUMENTS 3,879,262  4/1975  Schuurs et al. ...................... 436/530

Primary Examiner—Robert J. Warden
Assistant Examiner—Stephen C. Wieder
Attorney, Agent, or Firm—John P. White

[57] ABSTRACT

There are provided magnetic and non-magnetic agarose and agar polyaldehyde beads with diameters ranging from 40 microns up to 1 cm, and processes for the synthesis of such beads. The polyaldehyde compounds e.g. polyacrolein, polymethacrolein or polyglutaraldehyde, were used as microspheres or as powders. The agarose-polyaldehyde beads are capable of covalently binding in a single step, through their aldehyde groups, compounds containing primary amino groups or thiol groups, such as proteins, antibodies, enzymes and drugs. The beads are useful for various biological applications e.g. affinity chromatography, hemoperfusion, ion exchange resins, cell labeling, diagnostic purposes and cell separation.

8 Claims, 4 Drawing Sheets

METHOD FOR REMOVING COMPONENTS OF BIOLOGICAL FLUIDS

This is a division of application Ser. No. 462,315, filed Jan. 31, 1983, abandoned.

BACKGROUND OF THE INVENTION

Polymerization of glutaraldehyde, acrolein and acrolein type compounds (e.g. methacrolein) under certain conditions results in the formation of the appropriate polyaldehyde polymers. Polymerization under the same conditions in the presence of appropriate surfactants produced these polyaldehyde polymers in microsphere shape.

Polyacrolein and polyglutaraldehyde powders as well as microspheres were used for binding covalently at physiological pH in a single step various compounds containing primary amino groups (e.g. proteins, antibodies and drugs). The Schiff base product can be reduced further with NaBH$_4$ or NaCNBH$_3$ to produce the stable C-N bond.

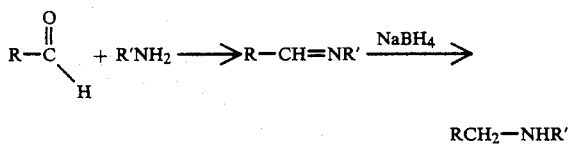

The aldehyde groups of the polymers interact also with thiol groups to form hemithioacetal products which under acidic conditions interact further to give the thioacetal products

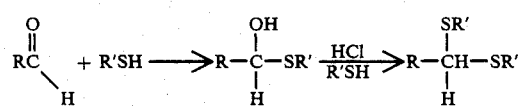

The polyaldehyde microspheres in various sizes were encapsulated with agarose, a blood compatible polymer of high porosity. The produced agarose-polyaldehyde beads were found to be suitable for various biological applications, such as cell labeling and cell separation, diagnosis, ion exchange resins, affinity chromatography and hemoperfusion.

SUMMARY OF THE INVENTION

The present invention relates to a novel synthesis of agarose-polyaldehyde beads or agar-polyaldehyde beads in various sizes (40 microns up to 1 cm) and to their biomedical uses. The beads were prepared by entrapping polyaldehyde compounds e.g. polyacrolein or polyglutaraldehyde in powder or microsphere form in molten agarose or agar which by appropriate cooling produce the beads. Magnetic beads were formed by entrapping magnetic particles in the molten agarose. FIG. 1 is a light microscopy picture of polyglutaraldehyde (a) and polyacrolein (b) powders encapsulated by agarose. FIGS. 2a to 2d are light microscopy pictures of beads with increasing concentration of polyacrolein microspheres (0.1 micron diameter) entrapped in agarose. FIG. 3a is a cross-sectional picture, obtained by transmission electron microscopy, of polyacrolein microspheres (0.2 micron diameter) entrapped by agarose, while FIG. 3b shows such beads containing magnetic particles of 0.03 micron diameter. Results obtained with agarose and with agar are substantially identical Beads according to the invention generally comprise from 2% agarose by weight of the beads up to 6% by weight of the beads; generally the polyaldehyde comprises up to about 10% by weight of the beads. Polyaldehyde such as polyacrolein, polyglutaraldehyde, starch dialdehyde and polyacrolein type compounds (e.g. polymethacrolein), in powder or in sphere form can be used. The agarose (or agar)-polyaldehyde beads can be cross linked. The matrix may also contain magnetic particles. The beads are generally of a diameter from about 40 microns to about 1 cm. The process for the production of agarose (or agar)-polyaldehyde beads comprises preparing aqueous solution containing agarose (or agar) and polyaldehyde powder (or microspheres), at an elevated temperature, introducing this mixture into a stirred hot oil, cooling the oil-water system and purifing the thus produced agarose-polyaldehyde beads from the oil. Several other similar processes for producing the beads are also described in the examples.

The beads are capable of binding through their aldehyde groups, proteins, antibodies, lectins, enzymes, drugs or any other compounds containing primary amino groups or thiol groups. The effect of binding spacers to the beads was studied and showed higher capacity of the beads toward the ligands bound through the spacer.

The agarose-polyaldehyde beads are blood compatible and have high porosity. They are useful for various biological applications, such as cell labeling, cell separation, diagnostic purposes, ion exchange resins, immobilization purposes, affininty chromatography and hemoperfusion.

The invention also contemplates the replacement of agarose with other polymers such as natural polymers (e.g. gelatin and dextrane), polymers prepared by addition polymerization (e.g. polymethyl methacrylate) and polymers prepared by condensation polymerization (e.g. nylons).

The invention also contemplates the replacement of the polyaldehyde microspheres with other polymeric microspheres e.g. polystyrene microspheres, polyacrylamide microspheres (cross linked), etc.

BRIEF DESCRIPTION OF THE FIGURES

The invention is illustrated with reference to the enclosed figures, in which.

Figure 1A:
FIG. 1 illustrates a light microscopy picture of polyglutaraldehyde and polyacrolein powders encapsulated by 4% agarose.
  a. agarose-polyglutaraldehyde (X200);
  b. agarose-polyacrolein (X300).
Figure 1B:
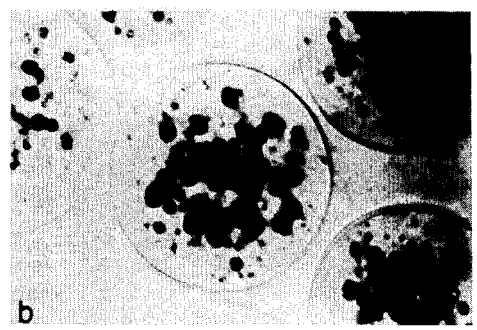
Figure 2A:
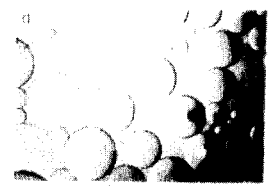
FIG. 2 illustrates a light microscopy picture (X200) of increasing concentration of polyacrolein microspheres (0.1 micron size) encapsulated by 4% agarose.
  a. without polyacrolein microspheres
  b. 0.25% polyacrolein microspheres;
  c. 1.0% polyacrolein microspheres;
  d. 7.0% polyacrolein microspheres.
Figure 2B:
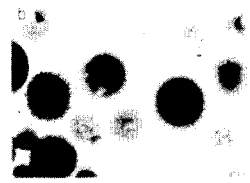
Figure 2C:
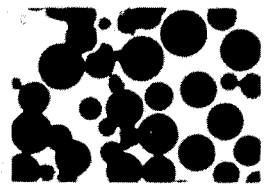
Figure 2D:
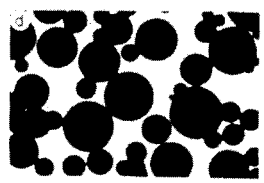
Figure 3A:
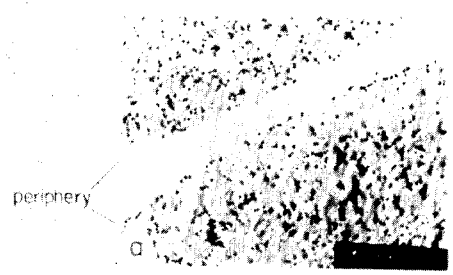
FIG. 3 illustrates a transmission electron microscopy picture describing:
  a. a cross section of agarose-polyacrolein beads (5% micrdspheres of 0.2 micron size, X3,300).
  b. a cross section of agarose-magnetic polyacrolein beads (5% microspheres of 0.2 micron size and 5% perrofluid, X55,000).
Figure 3B:
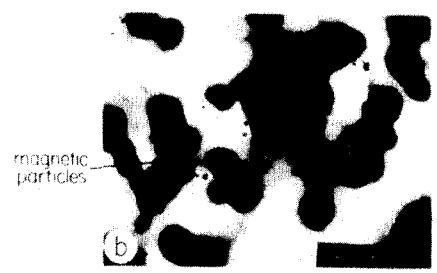

The following examples are of an illustrative nature only, and are not to be construed in a limitative manner.

EXAMPLE 1

Preparation of Agarose-Polyacrolein Beads
Encapsulation of Polyacrolein Powder

A solution containing 0.8 gr agarose and 20 ml distilled water (4% w/v) was heated to 95° C. until the gel melted into a clear solution. The temperature was then decreased to 70° C. and 1.25 gr of polyacrolein powder was added to the stirred solution. The stirring was continued for another ½ an hour and the solution was then poured into 100 ml of stirred (with a mechanical stirrer, at 300 rpm) peanut oil at 70° C. Ten min. later, the solution was cooled with ice The beads produced were purified from the peanut oil with ether. The ether was then removed by evaporation. The produced beads were found to have diameters ranging from 40 microns up to 150 microns and were stored at 4° C. in water or in phosphate buffered solution (PBS, 0.1M, pH-7.2), in the presence of 0.05% (w/v) sodium azide.

The diameter of the beads is dependent on the viscosity of the oil solution. Increasing the viscosity leads to a decrease of the average diameter of the beads. For example: Increasing (1) the agarose concentration, (2) the polymer concentration, (3), the temperature of the oil or (4) the viscosity of the oil will lead to a corresponding decrease in the average diameter of the beads. Furthermore, the size of the beads is also dependent on the stirring rate of the oil. Increasing the stirring rate, decreases the diameter of the beads.

EXAMPLE 2

Preparation of Agarose-Polyacrolein Beads, Encapsulation of Polyacrolein Microspheres The procedure of Example 1 was repeated substituting polyacrolein microspheres of 0.1 micron size (4% w/v), in place of the polyacrolein powder. The diameter of the beads produced ranged from 40 microns up to 150 microns. The diameter of the beads can be controlled as described in example 1.

EXAMPLE 3

The procedure of Example 2 was repeated substituting polyacrolein microspheres of 0.4 micron size instead of the polyacrolein microspheres of 0.1 micron average diameter. The produced beads were of sizes ranging from 200 microns up to 1 mm.

EXAMPLE 4

The procedure of Examples 1 to 3 was repeated substituting 2% (w/v) and 6% (w/v) agarose, respectively in place of 4% (w/v). The beads with 2% (w/v) were softer and smaller in their average diameter than those obtained with 4% (w/v) agarose. On the other hand the beads with 6% (w/v) were harder and larger in average diameter.

EXAMPLE 5

The procedure of example 2 was repeated, substituting polyacrolein microspheres of 9% (w/v) in place of 4% (w/v). The beads produced were of sizes ranging from 300 microns up to 1 cm.

EXAMPLE 6

Preparation of Magnetic Agarose-Polyacrolein Beads

Example 2 was repeated in the presence of Ferrofluid-5% (w/v) ($Fe_3O_4$ particles). Magnetic beads in sizes ranging from 40 microns up to 150 microns were obtained.

EXAMPLE 7

Preparation of Agarose-Polyacrolein Beads by Polymerizing Acrolein in Agarose Beads (Sepharose)

A solution containing 20 ml of sepharose 4B, 23 ml of 0.5% (w/v) polyethylene oxide aqueous solution and 2.5 ml acrolein was deaerated with argon. The stirred solution was then irradiated with a cobalt source (0.75 megarad). The produced agarose (sepharose)-polyacrolein beads were washed free of the non-encapsulated microspheres by repeated decantation with water and then stored at 4° C. in the presence of 0.05% (w/v) sodium azide.

EXAMPLE 8

Preparation of Agarose-Polyacrolein Beads by Polymerizing Acrolein in Molten Agarose A solution containing 0.8 gram agarose and 20 ml of 0.5% (w/v) polyethylene oxide aqueous solution was heated to 95° C. until the gel was melted into a clear solution. The temperature was then decreased to 50° C. and 2.5 ml acrolein, 150 mg ammonium persulfate and 50 mg thioglycolic acid were added. The polymerization of acrolein in the melted agarose was continued for 5 hours. The solution was then poured into 100 ml of stirred peanut oil (at 300 rpm) at 70° C. The procedure was then continued as described in Example 1. The beads formed ranged from 40 to 300 microns.

EXAMPLE 9

Example 8 was repeated substituting $H_2O$ in place of 0.5% (w/v) polyethylene oxide aqueous solution. The beads obtained had similar sizes (40 to 300 microns).

EXAMPLE 10

Preparation of Agarose-Polyacrolein Beads by The Syringe Method

A solution containing 0.8 gr agarose and 10.0 ml $H_2O$ was heated to 95° C. until the gel was melted into a clear solution. 10.0 ml of aqueous polyacrolein microspheres (10% w/v, 0.1 micron size) solution were then added to the stirred solution. 10 minutes later, the solution was drawn into a 40 ml syringe and was immediately injected dropwise into an ice-cold organic solvent mixture composed of toluene (100 ml), chloroform (40 ml) and hexane (20 ml). The beads obtained were of uniform diameter ($\pm 10\%$). The size of the beads could be varied from 100 microns up to 1 cm by altering the injection rates or the gauge of the syringe needle. The beads were poured onto a sieve, then washed with 1,4-dioxane and finally with $H_2O$. Then, they were stored at 4° C. in the presence of 0.05% (w/v) sodium azide.

EXAMPLE 11

Preparation of Agarose-Polyglutaraldehyde Beads

Examples 1 to 6 were repeated substituting glutaraldehyde in place of acrolein. The beads obtained had similar sizes, respectively.

EXAMPLE 12

Preparation of Agarose-Polyglutaraldehyde Beads by Polymerizing Glutaraldehyde in Molten Agarose A solution containing 0.8 gram agarose and 17.5 ml distilled water was heated to 95° C. until the gel was melted into a clear solution. The temperature was then decreased to 70° C. and 7.5 ml of glutaraldehyde aqueous solution (50%) was added. NaOH solution (10N) was then added until a pH of 10.0 was reached. The polymerization of glutaraldehyde in the molten agarose was continued for 2 hours. The solution was then poured into 100 ml of stirred peanut oil (at 300 rpm) at 70° C. The procedure was then continued as described in example 1. The beads obtained had sizes ranging from 40 microns to 150 microns.

Uniform beads with sizes varied from 100 microns up to 1 cm were obtained by injecting the agarose-polyglutaraldehyde solution through a syringe needle into organic solvents, as described in example 10.

EXAMPLE 13

Preparation of Agarose-Polyglutaraldehyde Beads by the Syringe Method

Example 10 was repeated substituting polyglutaraldehyde microsphres (0.1 micron size), in place of polyacrolein microspheres. The size of the beads is also controlled as described in example 10.

EXAMPLE 14

Preparation of Agarose-Polymethacrolein Beads

Examples 1 to 10 were repeated substituting methacrolein instead of acrolein. The beads obtained had similar sizes, respectively.

EXAMPLE 15

Preparation of Agarose-Starch Dialdehyde Beads

Example 1 was repeated in the presence of starch dialdehyde instead of polyacrolein. The beads obtained had a similar size range.

EXAMPLE 16

Preparation of Agar-Polyaldehyde Beads

Example 1 to 10 were repeated substituting agar for agarose (Noble agar). Substantially identical results were obtained.

EXAMPLE 17

The procedure of Examples 1 to 16 were repeated substituting paraffin oil for the peanut oil. The produced beads were of sizes larger (about twice diameter) than those obtained with peanut oil, respectively.

EXAMPLE 18

Cross Linking of the Agarose Polyaldehyde Beads

Cross linking of the agarose polyaldehyde beads prepared as described in examples 1 to 17 was obtained by the following ways:

(a) A solution containing 1 gr beads, 2 ml 0.1N NaOH aqueous solution and 10 mg epichlorohydrin was shaken at 60° C. for 3 hour or at 25° C. for 12 hours. The beads were then washed with water or PBS by repeated decantation.

(b) A similar procedure to (a) substituting bis oxyrane in place of epichlorohydrin.

(c) A similar procedure to (a) substituting 1,2-dibromopropanol in place of epichlorohydrin.

(d) A solution containing 1 gr beads, 2 ml aqueous solution of pH 11.0 and 10 mg divinyl sulfone were shaken at 60° C. for 2 hours. The beads were then washed as described in (a).

EXAMPLE 19

Covalent Binding of Spacers to the Agarose-Polyaldehyde Beads 20 gram of the agarose-polyaldehyde beads prepared as described in examples 1 to 18 in 35 ml of distilled water were shaken for 24 hours with 40 mg of polylysine. The polylysine conjugated beads produced were washed free of unbound polylysine by repeated decantation with water. The beads solution (20 gr in 35 ml $H_2O$) was then shaken for 12 hours with 2 ml glutaraldehyde (50%) and the resultant polylysine-glutaraldehyde conjugated beads were filtered and then washed with a large quantity of distilled water. The binding of polylysine-glutaraldehyde to the magnetic beads was carried out in a similar procedure. The derivatized magnetic beads were washed free of unbound spacer by repeated decantation with water in the presence of a magnetic field.

EXAMPLE 20

The procedure of example 19 was repeated substituting the spacers, polyornithine, polyacrylhydrazide or hexane diamine in place of polylysine.

EXAMPLE 21

The procedure of example 19 was repeated substituting oxidized dextran (200 mg) in place of glutaraldehyde.

EXAMPLE 22

Binding of Drugs with Primary Amino Groups to the Agarose-Polyaldehyde Beads

Binding of Desferal (Iron Chelating Reagent)

3 grams of the agarose-polyacrolein beads prepared as described in example 2 were shaken for 12 hours with 150 mg Desferal at 60° C., in 10 ml of an aqueous solution at pH 8.8 (with NaOH). Unbound Desferal was removed from the bound Desferal by repeated decantation with water. Spectrophotometric measurements showed that 85% of the Desferal was bound to the beads. A further reduction of the Schiff base product was then carried out by adding 0.5 mg $NaBH_4$ to a shaken solution (room temperature) of the beads in 10 ml PBS. 3 hours later the beads were washed several times by repeated decantation with water.

The beads were then shaken for ½ with 10 ml of normal human serum poisoned with 10 ppm $FeCl_3$. Spectroscopic measurements showed that the iron compound was quantitatively removed from the serum to the beads.

EXAMPLE 23

Binding of Lectins to the Agarose-Polyaldehyde Beads

Binding of Concanavalin A and Soybean Agglutinin 1 gram of the agarose-polyacrolein beads prepared as described in Example 2 with and without a bound spacer (polylysine-glutaraldehyde) were shaken for 12 hours at room temperature in 5 ml PBS with 25 mg of either Con A or soybean agglutinin. Unbound lectins were separated from bound by repeated decantation with water. Spectrophotometric measurements showed that 10 mg of the Con A and 5.9 mg of Soybean Agglutimin were bound to the beads with a bound spacer, and 3 mg of each Con A and Soybean Agglutinin were bound to the beads without the spacer.

EXAMPLE 24

Binding of Hormones to the Agarose-Polyaldehyde Beads

Binding of Bovine Insulin

Example 23 was repeated substituting bovine insulin (25 mg) in place of the lectins. 22 mg insulin were bound to beads with a spacer and 7.2 mg to beads without the spacer.

EXAMPLE 25

Binding of Antibodies to the Agarose-Polyaldehyde Beads

Binding of Goat Anti-Mouse Ig (gxmIg) and Monoclonal Anti-Mouse Thy 1.2

Example 23 was repeated substituting gxmIg and anti-mouse Thy 1.2 in place of the lectins. 12.4 mg of gxmIg and 9.8 mg of anti-mouse Thy 1.2 were bound to the beads with a spacer, while 2.4 mg gxmIg and 2.5 mg of anti-mouse Thy 1.2 were bound to the beads without the spacer.

EXAMPLE 26

Binding of Enzymes to the Agarose-Polyaldehyde Beads

Binding of Chemotrypsin

Example 23 was repeated substituting chemotrypsin in place of the lectins. 3 mg of the enzyme were bound to the beads without the spacer and 8 mg to the beads with the spacer.

EXAMPLE 27

Binding of proteins to the Beads

Binding of Bovine Serum Albumin (BSA), Dinitrofluorebenzene-,BSA (DNP-BSA) and Rabbit Immunoglubulin (RIgG)

The conditions and the results of these reactions are summarized in Tables 1, 2 and 3.

EXAMPLE 28

Binding of Thio-Compounds to the Agarose-Polyaldchyde Beads

Binding of Thioglycerol 1 gram of the agarose-polyacrolein beads prepared as described in examples 1 to 6 were shaken with 100 mg thioglycerol for 12 hours at room temperature in 5 ml $H_2O$. Unbound thioglycerol was separated from the bound thioglycerol by repeated decantation with water. When the reagent dinitrophenyl hydrazine was added to the beads solution no colour was obtained, while by adding the same reagent to the beads which did not react with thioglycerol, intense orange colour was obtained, indicating that all the aldehyde groups were bound to the thioglycerol.

Binding of Pentaeryheritol Tetrathioglycolate 3 grams of the agarose-polyacrolein beads prepared as described in examples 1 to 6 were shaken with 0.5 gr of pentaerythritol tetrathioglycolate for 12 hours at room temperature in 10 ml dimethylformamide. Unbound pentaerythritol tetrathioglycolate was then removed by repeated decantation with dimethyl formamide and then with water.

The conjugated beads were then shaken for ½ hour with 10 ml of normal human blood poisoned with 3 ppm $CH_3HgCl$. Atomic absorption measurements showed that 90% of the mercury compound was removed from the blood by the conjugated beads.

EXAMPLE 29

The Use of Agarose-Polyaldehyde Beads for Affinity Chromatography

Model System: Purification of Rabbit Anti-BSA 1 gram of the agarose-polyacrolein beads prepared as described in example 2, with and without a bound spacer (polylysine-glutaraldehyde) were shaken for 24 hours at room temperature with 20 mg BSA in 10 ml PBS. Unbound BSA was then removed by repeated decantation with PBS. The remaining aldehyde groups were then blocked by shaking the beads for 12 hours with 100 mg ethanolamine in an aqueous solution, adjusted to pH-7.2 with HCl. The beads were then washed successively with PBS, eluting medium (0.2M glycine-HCl buffer, pH-2.4) and again with PBS.

Rabbit anti BSA was purified and isolated by passing whole immune serum (usually 5–10 ml) through a column containing the immunoabsorbent (BSA bound to the beads). The immunoabsorbent was then washed several times with PBS. Rabbit anti BSA was then eluted with 0.2M glycine-HCl buffer pH-2.4, neutralized with NaOH and dialysed against PBS. The purified antibody was then submitted to analysis by gel immunoelectrophoresis and was found to contain only IgG. The immunoabsorbent, after treatment with glycine-HCl was washed several times with PBS and stored at 4° C. until reused. This immunoabsorbent was used repeatedly over a period of 6 months without any significant loss of antibody binding capacity.

The specificity of the immunoabsorbent was also checked by passing normal rabbit serum through the immunoabsorbent. The immunoabsorbent was then treated in the same way as was described for the isolation of the rabbit anti BSA. Under these conditions no proteins were eluted from the immunoabsorbent.

The results describing the binding capacity of BSA and the isolation of rabbit anti BSA are shown in Table 4.

EXAMPLE 30

Example 29 was repeated substituting polyacrylhydrazide-glutaraldehyde as a spacer in place of polylysine-glutaraldehyde.

The results obtained for the binding capacity of BSA and for the isolation of rabbit anti BSA are shown in Table 4.

EXAMPLE 31

Examples 29 and 30 were repeated substituting agarose-polyglutaraldehyde beads prepared as described in example 11 in place of the agarose-polyacrolein beads.

The results obtained for the binding capacity of BSA and for the isolation of rabbit anti BSA are shown in Table 4.

EXAMPLE 32

Examples 29, 30 and 31 were repeated substituting the magnetic beads prepared as described in example 6 in place of non-magnetic beads. The work was carried out batchwise and the separation of ligands bound to the beads from free ligands was achieved by attracting the beads with a magnet to the wall of a vial and decantating the supernatant. The attracted beads were resuspended with PBS and the magnetic separation was repeated twice.

The results obtained for the binding capacity of BSA and for the isolation of rabbit anti BSA are shown in Table 4.

EXAMPLE 33

Example 29 was repeated substituting agarose-polyglutaraldehyde beads prepared as described in example 11 in place of agarose-polyacrolein beads, the spacer polylysine-oxidized dextran (20%) in place of polylysine-glutaraldehyde, RIgG and goat anti-rabbit IgG in place of BSA and rabbit anti-BSA.

The results for the binding capacity of the beads towards rabbit IgG and for the isolation of goat anti rabbit IgG are shown in Table 4.

EXAMPLE 34

The Use of Agarose-Polyaldehyde Beads for Hemoperfusion purposes

Figure 4:
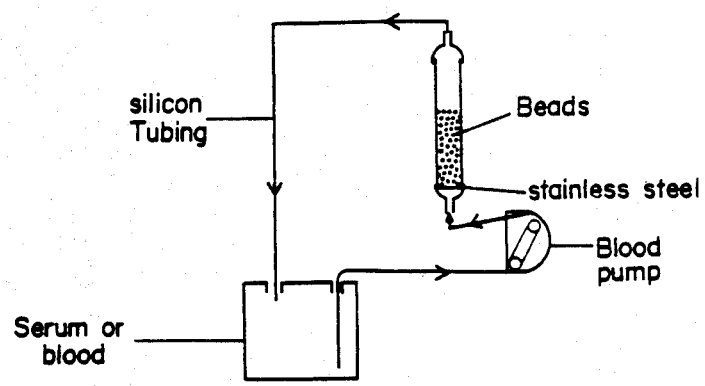
FIG. 4 illustrates the system employed for the removal of anti BSA from rabbit serum or whole blood.
Figure 5:
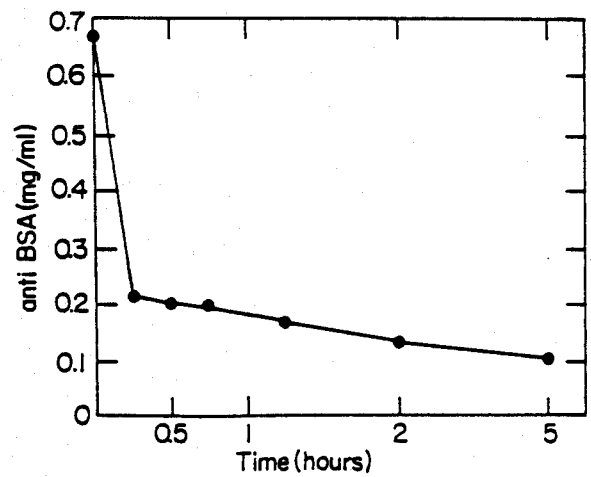
FIG. 5 illustrates the rate of the removal of anti BSA from an immunized rabbit serum or whole blood.

Purification of Anti BSA from Rabbit Serum and Blood 100 ml of an immunized rabbit anti BSA serum was circulated in a flow rate of 55 ml/min through a column containing 18 grams agarose (4%w/v) polyacrolein microspheres prepared as described in example 3 (FIG. 4). The beads were bound to polylysine-glutaraldehyde-BSA (10 mg BSA/gram beads). During the circulation fractions were collected and checked by radio immuno assay for rabbit anti BSA. The results for this kinetic run are illustrated in FIG. 5. The rabbit anti BSA bound to the column was eluted (60 mg) with 0.2M glycine-HCl buffer, pH-2.4.

Running of whole blood under the same conditions produces the same results for the removal of the rabbit anti BSA, while during the first 4 hours run hemolysis of the red blood cells and loss of lymphocytes were negligible and platelet loss was 20%.

In Vivo experiments with immunized rabbits showed similar results as obtained in the In Vitro experiments (Table 5).

EXAMPLE 35

The Use of Agarose-Polyaldehyde Beads for Cell Separation

A Model—Separation of Human Red Blood Cells from Turkey, Red Blood Cells 1 gram of magnetic beads prepared as described in example 6 with a spacer of polylysine-glutaraldehyde bound, were shaken at 4° C. for 3 hours in ml PBS with 1 mg of goat antirabbit IgG. The immunobeads produced were separated from unbound antibody by attracting the beads with a magnet to the wall of a vial and decantating the supernatant. The attracted beads were resuspended with PBS and the magnetic separation was repeated twice. The remaining aldehyde groups were blocked by shaking the immunobeads (12 hrs) with ethanol amine (100 mg at pH-7.2). The immunobeads were then washed free of excess ethanolamine by using a magnetic field as described previously.

Human RBC from a normal donor, fixed with 3% glutaraldehyde were sensitized with rabbit anti human RBC. The RBC ($5 \times 10^7$) suspended in 0.5 ml of PBS containing 0.2 mg rabbit anti-human RBC were agitated for 30 min and the cells were separated and washed 3 times by centrifuging the PBS suspension at $500 \times g$ for 10 min.

A mixture of turkey RBC and sensitized human RBC ($5 \times 10^7$ of each type suspended in 2 ml PBS) was filtered at room temperature at a rate of 10 drops/min through a packed column of the immunobeads. The nonabsorbed cells contained 95% turkey RBC. The beads in the column were then poured into a beaker, 5 ml of PBS was added and the adsorbed cells were recovered by gently stirring the beads with a Pasteur pipette. The eluted cells were separated from the beads with a magnetic field as described previously. The cells eluted from the beads contained 95% human RBC.

EXAMPLE 36

Example 35 was repeated substituting the non-magnetic beads prepared as described in example 2 in place of the magnetic beads. The separation of beads bound to ligands from unbound ligands was achieved by repeated decantation of the supernatant with PBS.

The results obtained in this experiment were similar to that which obtained in example 35.

EXAMPLE 37

Fractionation of B and T mouse Splenocytes

Agarose-polyacrolein beads (150 microns to 250 microns size) bound to either gxmIg. anti-Thy 1.2 or soybean agglutinin were packed in a siliconized pasteur pipette plugged with glass wool. The beads were washed first with PBS and then with Hank's solution containing 5% horse serum (HS). Washed, viable cells ($1-2 \times 10^7$) suspended in 1-2 ml of Hank's+5% HS were filtered through the immuno-beads (1 gr) at room temperature, at a rate of 1-3 drops/min. The column was then rinsed with Hank's+5% HS till the eluate became cell-free. Non-adsorbed cells were recovered by centrifugation at $500 \times g$ for 15 minutes and then resuspended in 1-2 ml of Hank's+5% HS. The beads were poured into a glass vial containing approximately 5 ml of Hank's+5% HS and the adsorbed cells were then recovered by gently stirring the beads with a pasteur pipette. Cells adsorbed to soybean agglutinin conjugated beads were recovered by passing 0.2M D-galactose in Hank's solution (3-5 ml) through the column. The supernatant containing the cells was centrifuged at $500 \times g$ for 15 minutes, and the cells were then resuspended in 0.5 ml of Hank's+5% HS. The immunobeads were washed with PBS and then stored in PBS+0.05% (w/v) sodium azide until reused. The fractionation results are shown in Table 6.

EXAMPLE 38

The Use of Agarose-Polyaldehyde Beads for Diagnostic Purposes

Measuring the Concentration of Anti BSA in Immunized Rabbit Serum. 5 ml of whole immunized rabbit serum was passed at a rate of 0.5 ml/min through a column (2 grams) containing the agarose-polyacrolein beads prepared as described in example 2 bound to polylysine-glutaraldehyde and BSA (14 mg BSA/gram beads). The supernatant collected was checked and was found to be free of anti BSA. The rabbit anti BSA bound to the column was then eluted with 6 ml of 0.2M glycine-HCl buffer, pH-2.4, neutralized with NaOH and dialysed against PBS. The concentration of the anti BSA in the serum was found to be 2 mg/ml.

EXAMPLE 39

The Use of Agarose-Polyaldehyde Magnetic Beads for Diagnostic Purposes 5 ml of whole immunized rabbit serum were shaken for 5 min. with 2 grams of the magnetic agarose-polyacrolein beads prepared as described in example 6 bound to polylysine-glutaraldehyde and BSA (14 mg BSA/gram beads). The beads were then separated from the serum by attracting them to a magnet. The serum was found to be free of anti BSA. The anti BSA bound to the beads was then eluted by dispersing the beads with 6 ml of 0.2M glycine-HCl buffer, pH-2.4. The buffered solution was then separated from the beads with a magnet, neutralized and dialysed against PBS. The concentration of the anti BSA in the rabbit serum was found to be 2 mg/ml.

EXAMPLE 40

Determination of BSA by Radioimmuno Assay (RIA)

BSA in unknown amount is allowed to compete with a known amount of an $^{125}I$ labeled BSA for the binding sites of rabbit anti-BSA (RαBSA) bound to the magnetic agarose-polyacrolein beads prepred as described in example 6. The concentrations of the BSA were determined by comparing its competitive capacity to that of BSA standard of known concentration. The test is performed by incubating at room temperature the unknown sample of BSA, the BSA standards, the $^{125}I$ BSA and the RαBSA magnetic beads. Bound and free BSA are then separated by a magnetic field. The radioactivity of the solid phase is then measured in a gamma counter. The amount of bound radioactivity is inversely proportional to the amount of BSA presents in the sample. The procedure is as follows: (1) 100 μl of BSA standards (0, 0.02, 0.04, 0.1, 0.2, 0.5 mg) in duplicate were pipetted into tubes 1 to 12. (2) 100 μl of the unknown, in duplicate were pipetted into tubes 13 to 14. (3) 100 μl of BSA—$^{124}I$ solution (~5 μCi) were pipetted into all the tubes (1 to 14) (4) 50 μl of the RαBSA conjugated beads were pipetted into all the tubes (1 to 14). All the tubes were then shaken at room temperature for 45 minutes. Bound BSA was separated from unbound with a magnetic field. The tubes were then capped and the radioactivity of the pellets was measured in a gamma counter.

EXAMPLE 41

Preparation of Ion Exchange Resins

Cationic exchange resins were produced by oxidizing the aldehyde groups of the agarose-polyaldehyde beads to carboxylate groups. This was achieved by purging oxygen (12 hours) through a 0.1N sodium hydroxide aqueous solution (1 ml) of the beads (100 mg) prepared as described in examples 1, 2 and 11.

EXAMPLE 42

Cationic exchange resins were also obtained by the covalent binding of aminomethanesulfonic acid ($NH_2CH_2SO_3H$) to agarose-polyacrolein beads. This was achieved by shaking the beads prepared as described in examples 2 (100 mg in 2 ml $H_2O$) with 20 mg of the aminomethanesulfonic acid solution brought to pH 7.0, (room temperature, 24 hours). Unbound ligand was removed be repeated decantation with water. Approximately 10 mg $NH_2CH_2SO_3^-Na^+$ were bound to 1 gram beads.

EXAMPLE 43

Anionic exchange resins were obtained by the covalent binding of N,N-diethylaminoethylamine (DEAE) to the agarose-polyacrolein beads prepared as described in examples 2. The procedure was similar to that described in example 42. Approximately 5 mg DEAE were bound to 1 gram beads.

TABLE 1

Binding of BSA to the agarose-polyaldehyde beads.
1 gram beads were shaken wih BSA in 5 ml PBS for 24 hours at room temperature.

| Polyaldehyde | spacer bound to the beads | Quantity of BSA added (mg) | Quantity of BSA bound (mg) |
|---|---|---|---|
| Polyglutaraldehyde[1] | — | 10 | 1.3 |
| " | hexane diamine | 10 | 2.5 |
| " | polyornithine-glutaraldehyde | 10 | 5.7 |
| Polyglutaraldehyde[2] microspheres | — | 10 | 2.4 |
| " | polylysine-glutaraldehyde | 20 | 11.5 |
| " | polylysine-oxidized dextrane | 20 | 16.7 |
| " | polyacrylhydrazide-glutaraldehyde | 20 | 16.5 |
| Polyacrolein microspheres[3] | — | 10 | 2.2 |
| " | polylysine-glutaraldehyde | 20 | 14.8 |
| " | polylysine-oxidized dextrane | 20 | 16.7 |
| " | polacrylhydrazide-glutaraldehyde | 20 | 15.5 |
| " | polylysin-glutaraldehyde | 20 | 13.0 |
| Magnetic beads with polyacrolein microspheres[4] | — | 10 | 2.2 |
| " | polyacrylhydrazide- | | |

TABLE 1-continued

Binding of BSA to the agarose-polyaldehyde beads.
1 gram beads were shaken wih BSA in 5 ml PBS for 24 hours at room temperature.

| Polyaldehyde | spacer bound to the beads | Quantity of BSA added (mg) | Quantity of BSA bound (mg) |
|---|---|---|---|
| | glutaraldehyde | 20 | 14.0 |

[1]beads prepared as described in Example 11
[2]beads prepared as described in Example 11, microspheres size 0.4 micron
[3]beads prepared as described in Example 2
[4]beads prepared as described in Example 6

TABLE 2

Binding of DNP—BSA to the agarose-polyaldehyde beads.
1 gram beads were shaken with DNP—BSA in 5 ml PBS for 24 hours at room temperature

| Polyaldehyde | Spacer bound | Quantity of DNP—BSA added (mg) | Quantity of DNP—BSA bound (mg) |
|---|---|---|---|
| polyglutaraldehyde microspheres[1] | — | 10 | 1.5 |
| " | hexanediamine-glutaraldehyde | 10 | 2.3 |
| " | polylysine-glutaraldehyde | 10 | 9.1 |
| " | polylysine-oxidized dextrane | 10 | 9.4 |
| Polyacrolein microspheres[2] | — | 10 | 1.8 |
| " | hexane diamine-glutaraldehyde | 10 | 3.6 |
| " | polylysine-glutaraldehyde | 10 | 9.0 |
| " | polylysine-oxidized dextrane | 10 | 9.2 |

[1]beads prepared as described in Example 11, microspheres size - 0.4 micron
[2]beads prepared as described in Example 2.

TABLE 3

Binding of rabbit IgG to agarose-polyaldehyde beads.
1 gram beads were shaken with rabbit IgG in 5 ml PBS for 24 hours at room temperature.

| Polyaldehyde | Spacer bound to the beads | Quantity of RIgG added (mg) | Quantity of RIgG bound (mg) |
|---|---|---|---|
| Polyglutaraldehyde microsphres[1] | — | 12 | 1.0 |
| " | hexanediamine-glutaraldehyde | 12 | 1.1 |
| " | polylysine-glutaraldehyde | 12 | 5.4 |
| " | polyacrylhydrazide-glutaraldehyde | 12 | 9.3 |
| Polyacrolein microspheres[2] | — | 12 | 1.0 |
| " | hexanediamine-glutaraldehyde | 12 | 2.0 |
| " | polylysine-glutaraldehyde | 12 | 3.8 |
| " | polylysine-oxidized dextrane | 12 | 2.2 |
| " | polyacrylhydrazide-glutaraldehyde | 12 | 10.3 |
| Magnetic beads with polyacrolein microsphres[3] | polyacrylhydrazide-glutaraldehyde | 12 | 8.0 |

[1]beads prepared as described in Example 11, microsphres size 0.4 micron
[2]beads prepared as described in Example 2.
[3]beads prepared as described in Example 6.

TABLE 4

Isolation of antibodies with the agarose-polyadehyde immumoadsorbents (1 gram beads)

| Polyaldehyde | Spacer | Antigen | Quantity of bound antigen (mg) | Antiserum used | Quantity of bound antibody (mg) | Quantity of eluted antibody (mg) |
|---|---|---|---|---|---|---|
| Polyglutar-aldehyde microsphres[1] | Polylysine-glutaraldehyde | BSA | 11.5 | rabbit | 14 | 12.6 |
| " | Polyacrylhydrazide-glutaraldehyde | BSA | 16.5 | rabbit | 9 | 9.9 |
| " | Polylysine-oxidized dextrane | rabbit IgG | 3.4 | goat | 12 | 12 |
| Polyacrolein microsphres[2] | — | BSA | 2.2 | rabbit | 2.4 | 2.2 |
| " | Polylysine-glutaraldehyde | BSA | 14.8 | rabbit | 16.5 | 17.0 |
| " | Polyacrylhydrazide glutaraldehyde | BSA | 15.5 | rabbit | 12.0 | 10.0 |
| Magnetic beads containing | — | BSA | 2.2 | rabbit | 3.0 | 4.0 |

TABLE 4-continued

Isolation of antibodies with the agarose-polyadehyde immumoadsorbents (1 gram beads)

| Polyaldehyde | Spacer | Antigen | Quantity of bound antigen (mg) | Antiserum used | Quantity of bound antibody (mg) | Quantity of eluted antibody (mg) |
|---|---|---|---|---|---|---|
| polyacrolein microspheres[3] | | | | | | |
| " | Polyacrylhydrazide glutaraldehyde | BSA | 14.0 | rabbit | 15.0 | 17.5 |

[1]beads prepared as described in Example 11, microspheres size 0.4 micron
[2]beads prepared as described in Example 2
[3]beads prepared as described in Example 6.

TABLE 5

Kinetics of adsorption of anti-BSA from an immunized rabbit, In Vivo experiment, column contained 30 gram beads conjugated to 150 mg BSA, pump speed - 10 ml/min.

| Time (min.) | Anti-BSA (mg/mg blood) |
|---|---|
| 0 | 1.45 |
| 15 | 0.75 |
| 30 | 0.55 |
| 45 | 0.40 |
| 60 | 0.32 |
| 75 | 0.27 |
| 90 | 0.25 |
| 120 | 0.22 |
| 150 | 0.20 |
| 180 | 0.19 |

TABLE 6

Cell fractionation of mouse splenocytes with immuno agarose-polyacrolein beads.

| | Percentage of Cells | | | | | |
|---|---|---|---|---|---|---|
| | Before fractionation | | After fractionation | | | |
| | | | Adsorbed cells | | Non-adsorbed cells | |
| Ligands bound to the beads | B cells | T cells | B | T | B | T |
| GαRIgG—APAMB (control) | 53 | 43 | | | 51 | 45 |
| GαMIg | 60 | 40 | — | —[1] | 0 | 98 |
| GαMIg | 58 | 40 | — | —[1] | 0 | 97 |
| anti-Thy 1.2 | 57 | 40 | 40 | 54 | 86 | 13 |
| anti-Thy 1.2 | 59 | 40 | 37 | 54 | 84 | 14 |
| soybean agglutinin | 57 | 38 | 84 | 16 | 15 | 77 |
| soybean agglutinin[2] | 56 | 41 | 84 | 16 | 17 | 81 |
| | | | 17 | 81 | 10 | 90 |
| | | | 10 | 90 | 7 | 90 |

[1]Small aggregates of o cells make cell counting inefficient.
[2]The non-adsorbed cells were passed through the immuno-beads 3 times.

I claim:

1. A method of removing a component from a biological fluid which comprises (a) contacting the fluid with substantially spherical, agarose-polyaldehyde beads, each of the beads having a diameter between 40 μm and 2 cm and comprising a polymer which binds to the component and which contains aldehyde groups, the polymer being in the form of substantially uniform microspheres and being a polyacrolein-type compound, polyglutaraldehyde or starch dialdehyde, the microspheres being encapsulated within an aqueous homogeneous, porous matrix of agarose or agar gel, the aldehyde groups of the polymer being bound to a compound containing at least one primary amine or thiol group by means of such amine or thiol group, and the compound to which the polymer is bound being capable of binding to the component to be removed from the fluid, so that the polymer binds to the component; and (b) removing the beads containing the polymer to which the component is bond from the fluid, and thereby removing the component from the biological fluid.

2. A hemoperfusion method of claim 1, wherein the biological fluid is blood.

3. A method of claim 1, further comprising treating the beads removed from the biological fluid so as to recover the component from the beads.

4. A method of claim 1, wherein the component is an ion.

5. A method of claim 1, wherein the compound is a protein.

6. A method of claim 5, wherein the protein is an antibody.

7. A method of claim 1, wherein the polymer is polyacrolein.

8. A method of claim 1, wherein the agarose or agar gel is cross-linked to itself.

* * * * *